United States Patent [19]

Pace et al.

[11] 4,396,014
[45] Aug. 2, 1983

[54] THUMB-SUCKING DISCOURAGEMENT DEVICE

[76] Inventors: Michael Pace; Alice L. Pace, 661 Sherwood Dr. B-1, both of Jonesboro, Ga. 30236; Frank Van Haltern, 1670 Montcliff Ct., Decatur, Ga. 30033

[21] Appl. No.: 233,918

[22] Filed: Feb. 12, 1981

[51] Int. Cl.³ .............................................. A61F 13/00
[52] U.S. Cl. .................................................... 128/133
[58] Field of Search ................................ 128/133, 252

[56] References Cited

U.S. PATENT DOCUMENTS

| | | | |
|---|---|---|---|
| 490,733 | 1/1893 | Armat | 128/133 |
| 1,048,569 | 12/1912 | Mitchell | 128/133 |
| 1,584,999 | 5/1926 | Thompson | 128/133 |
| 1,652,867 | 12/1967 | MacLaclan | 128/133 |
| 1,929,318 | 10/1933 | Klosky | 128/133 |
| 2,303,675 | 12/1942 | Berghs | 128/133 |
| 2,617,413 | 11/1952 | Belknap | 128/133 |
| 2,633,126 | 3/1953 | Newmark | 128/133 |
| 2,798,482 | 7/1957 | Feeney | 128/133 |
| 3,415,244 | 12/1968 | Block | 128/133 |

*Primary Examiner*—Michael H. Thaler
*Assistant Examiner*—C. W. Shedd
*Attorney, Agent, or Firm*—Jones & Askew

[57] ABSTRACT

A device which discourages thumb-sucking when worn on a thumb. The device comprises an elongate sleeve which fits over the thumb. An air passageway which extends from one end of the sleeve to the other is formed therein. A flange extending outwardly from the sleeve prevents both ends of the air passageway from being insertable into the mouth. Straps attached to the sleeve removably retain the device on the thumb.

6 Claims, 3 Drawing Figures

U.S. Patent     Aug. 2, 1983     4,396,014
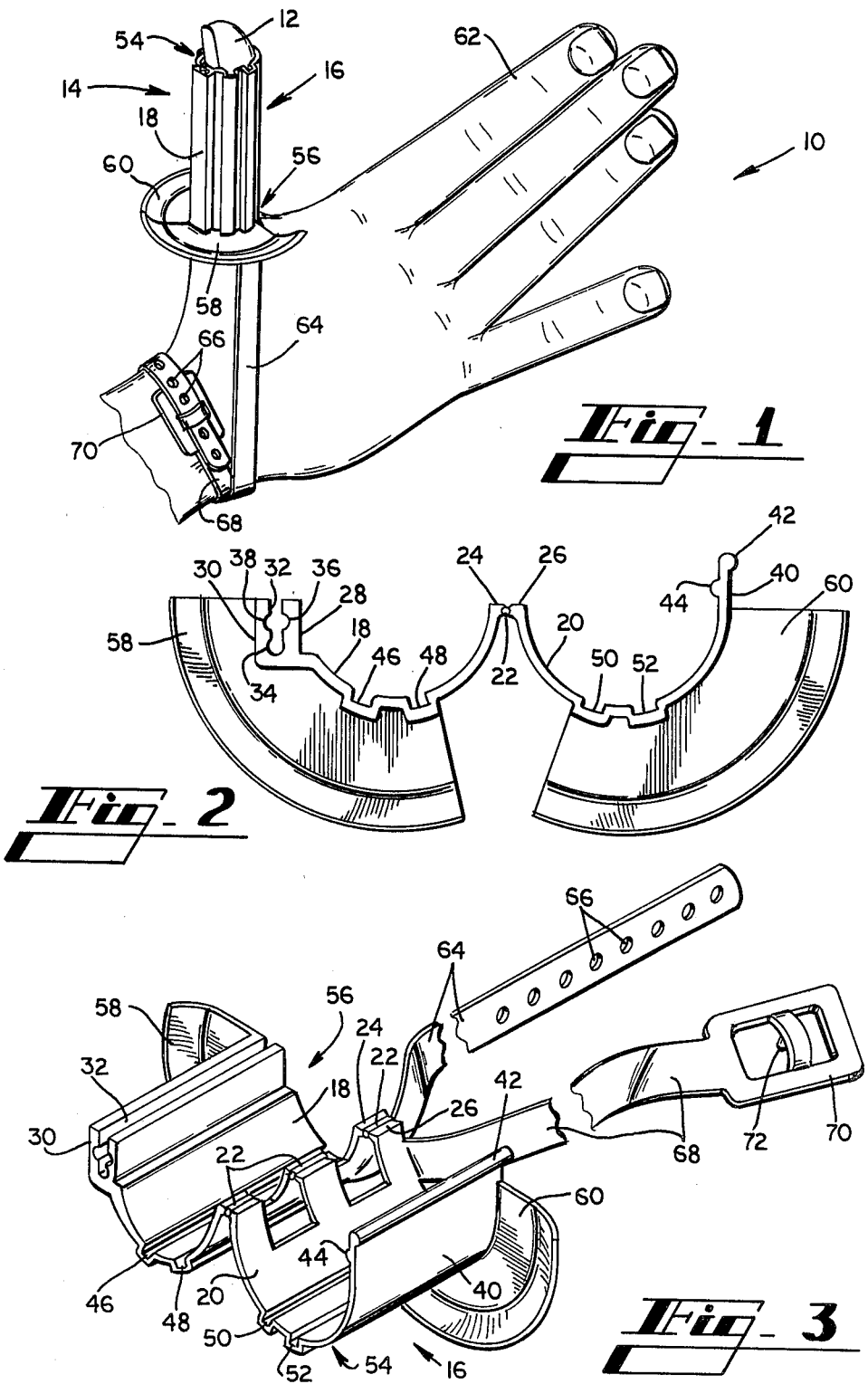

THUMB-SUCKING DISCOURAGEMENT DEVICE

TECHNICAL FIELD

The present invention relates to a device which discourages thumb-sucking, and, more particularly, to such a device which is wearable on the thumb of a child which device does not substantially restrict movement of the thumb or hand when worn.

BACKGROUND

Thumb-sucking is a frequently encountered habit adopted by children typically from the time the child is weened from the bottle until the age of five or six. However, in some instances the habit can extend into the later years of child development.

Thumb-sucking is an undesirable activity for children, not only because of the psychological affect commonly associated therewith, but also from a physiological standpoint. Thumb-sucking is often a causal or contributing factor to the development of malocclusion in children. The frequent presence of the thumb in a child's mouth, particularly while sleeping, exerts an outward force on the upper teeth and an inward force on the lower teeth, thus producing an overbite condition. Such a condition not only effects the normal chewing function of the teeth but often induces malformation of the surrounding facial features.

Breaking the thumb-sucking habit has long been recognized as a necessity to the normal physical and psychological development of a child. However, accomplishing the same is sometimes a difficult and ofter a frustrating experience. Various chemical and mechanical devices have been developed in an effort to aid in breaking or preventing the thumb-sucking habit. U.S. Pat. Nos. 2,225,896; 2,617,413; 1,929,318; 2,767,709; 2,972,348; 2,498,122; 2,633,126; 1,990,384; 2,357,413; 2,783,759; 2,742,898; 3,334,625 and 3,442,267 (all incorporated herein by reference) disclose various thumb-sucking preventive or discouragement devices.

Although it has been previously recognized that one method of discouraging thumb-sucking is to prevent the child from achieving a partial vacuum in its mouth while sucking on its thumb, none of the prior devices has been entirely successful. Some prior devices using this principal include a guard which fits over the thumb and includes a plurality of holes and/or ribs to form air channels therein. However, some of these devices are bulky, cumbersome and tend to restrict the free movement of the thumb. In others, it would be possible for the child to put the entire device in its mouth, thereby avoiding the air channels.

Accordingly, it is an object of the present invention to provide an improved device to discourage thumb-sucking.

Another object of the present invention is to provide a device to discourage thumb-sucking which device presents the drawing of a partial vacuum when sucked.

A further object of the present invention is to provide a device to discourage thumb-sucking which device does not substantially limit movement of the thumb or hand when worn.

Yet another object of the present invention is to provide a device to discourage thumb-sucking which device is relatively comfortable to wear.

These and other objects, features and advantages of the present invention will become apparent after a review of the following detailed description of the disclosed embodiment and the appended drawing and claims.

BRIEF DESCRIPTION OF THE DRAWING

FIG. 1 is a pictorial view of a disclosed embodiment of the thumb-sucking discouragement device of the present invention shown being worn on a hand.

FIG. 2 is an end view of the device shown in FIG. 3.

FIG. 3 is a pictorial view of the device shown in FIG. 1 with the device shown in an open position.

DETAILED DESCRIPTION OF THE DISCLOSED EMBODIMENT

Referring now to the drawing in which like numbers indicate like elements throughout the several views, it will be seen that there is a human hand 10 including four fingers and a thumb 12. A thumb-sucking discouragement appliance 14 is worn on the thumb 12 of the hand 10. The appliance 14 comprises an elongate sleeve 16 which fits over the thumb 12. The sleeve 16 can be formed of a single piece of material or it can be formed of two or more pieces which fit together to form the sleeve. Furthermore, the sleeve 16 can be a continuous piece of material from one end to the other or it can include openings which not only facilitate molding the sleeve in one piece, but which also provide ventilation of the thumb when the appliance is worn.

The sleeve 16 is comprised of two elongate members 18, 20. Each of the members 18, 20 has a cross-sectional shape which is substantially an open semi-circle. The two members 18, 20 are pivotally attached to each other by an integral hinge 22 formed in the plastic from which the two members are made along adjacent longitudinal edges 24, 26. Such integrally formed hinges are well known in the art. The hinge 22 is designed so that the member 20 can pivot about the hinge from the open position shown in FIGS. 2 and 3 to the closed position shown in FIG. 1. When the two semi-circular member 18, 20 are in the closed position, it will be appreciated that a substantially elongate cylindrical opening for receiving the thumb 12 is defined therebetween.

Formed on the longitudinal edge 28 of the member 18 which is opposite the hinge 22 is an enlarged portion 30 having a slot 32 and three grooves 34, 36, 38 formed therein. Formed on the longitudinal edge 40 of the member 20 opposite the hinge 22 are two projections 42, 44. It will be appreciated by those skilled in the art that when the members 18, 20 are in the closed position the projection 42 will snap fit into the groove 34 and the projection 44 will snap fit into the groove 36 thereby latching the two members in the closed position. The two members 18, 20 can also be returned to the open position by disengaging the projections 42, 44 from the grooves 34, 36.

Formed in the members 18 is a pair of channels 46, 48. Similarly, formed in the member 20 is a pair of channels 50, 52. The channels 46–52 extend longitudinally from the upper ends 54 of the members 18, 20 to the lower ends 56 of the members. It will be appreciated by those skilled in the art that the channels 46–52 provide air passageways which extend from one end of the sleeve 16 to the other. The cross-sectional shape of each of the channels 46–52 is substantially rectangular. The rectangular shape of the channels 46–52 makes it difficult to completely close off the channels to the passage of air with body tissue, such as by sticking the tongue into the ends of the channels. Although the present invention has been shown as using four channels or air passageways, it should be understood that any practical number of channels can be used as long as there is at least one such channel.

Extending radially outward from the base or lower end 56 of the member 18 is a flange 58. As best shown in FIG. 2, the flange 58 extrends circumferentially around the member 18 approximately 90°. Similarly, extending radially outwardly from the base or lower end 56 of the member 20 is a flange 60, which also extends circumferentially around the member 20 approximately 90°. As best shown in FIG. 1, when the two members 18, 20 are in the closed position, the two flanges 58, 60 abut to form a single flange which extends radially outwardly from the base of the sleeve 16 and extends circumferentially around the sleeve approximately 180°. Additionally, the flanges 58, 60 curve upwardly slightly from the base of the sleeve 16 toward the upper end 54 of the sleeve. Although this slight upward curve is preferred, it should be understood that the flange can also extend outwardly in a flat plane or it can curve downwardly slightly.

The flanges 58, 60 extend outwardly from the sleeve 16 a distance which is sufficient to prevent a child from inserting the entire lower end 56 of the sleeve and flanges 58, 60 into his mouth. Additionally, the circumferential extent of the flanges 58, 60 must be such that they do not interfere with the movement of the thumb. Therefore, it is desirable to omit the flange from the half of the sleeve which is adjacent the index finger 62 of the hand 10.

It should be noted that the channels 46–52 terminate at the lower end 56 of the sleeve 16 at a position below the flanges 58, 60. By positioning the channels and flanges in this manner, it is assured that both ends of the channels or air passageways cannot be inserted in the mouth simultaneously. The openings of the air passageways below the flange will always be open when the other end of the passageways are in the mouth. Therefore, it is virtually impossible to block off the air passageways in the sleeve to permit the establishment of a partial vacuum when the upper end of the sleeve is sucked.

Attached to the lower end of the member 18 is a strap 64 which is provided with a plurality of holes 66 along its length. Attached to the lower end of the member 20 is a strap 68 which is provided with a buckle 70. The buckle 70 includes a projection 72 which is operative to engage the holes 66 in a manner well known in the art. The straps 64, 68 are provided to temporarily retain the appliance 14 on the thumb 12.

Although the present invention can be made from most any suitable non-toxic plastic material, it is preferred that it be made from silicone rubber.

The operation of the appliance 14 will now be considered. The two members 18, 20 which are initially in the open position are pivoted about the hinge 22 to the closed position to form the sleeve 16. The edge 40 is inserted in the slot 32 and the projections 42, 44 are engaged with the grooves 34, 36. The sleeve 16 is then placed over the thumb 12 so that the upper end 54 of the sleeve is adjacent the tip of the thumb. The strap 64 is extended across the back of the hand 10 and wrapped around the wrist. The strap 68 is extended across the palm of the hand 10 and wrapped around the wrist. The end of the strap 64 is then threaded through the buckle 70 so that the projection 72 engages one of the holes 66.

When a child wearing the appliance 14 places his thumb in his mouth, he can only insert the sleeve 16 into his mouth up to the flanges 58, 60. Since the lower ends of the air passageways terminate below the flanges 58, 60 he cannot block them off with his mouth or tongue. Therefore, when the child sucks on the appliance 14 on his thumb 12, it is virtually impossible for the child to establish a partial vacuum. The inability to establish the partial vacuum eliminates the desired stimulus and over a relatively short period of time eliminates the desire itself.

Although the appliance 14 can be worn at any time, it is found that by wearing the appliance at night when the desire to suck the thumb is usually greatest is most effective. The appliance 12 can therefore be put on the thumb at bedtime and removed in the morning. Additionally, while the foregoing invention has been described as being worn on a thumb, it is specifically contemplated that the appliance can be worn on other fingers or digits of the hand.

The appliance 14 can be removed from the thumb 12 by disengaging the projection 72 from the holes 66, removing the strap 64 from the buckle 70, unwrapping the straps 64, 68 from the wrist and sliding the sleeve 16 off the end of the thumb. Additionally, for easy storage, the projectons 42, 44 can be disengaged from the grooves 34, 36 and the two members 18, 20 returned to the open position. This also facilitates cleaning of the inside of the sleeve 16.

It should be understood, of course, that the foregoing relates only to a preferred embodiment of the present invention and that numerous modifications or alterations may be made therein without departing from the spirit and scope of the invention as set forth in the appended claims.

We claim:

1. A device worn on a thumb for discouragement of thumb-sucking, said device comprising:
   an elongated sleeve having a base end and operative to be worn on said thumb such that said base end is remote from the distal tip of said thumb;
   an air passageway formed in said elongated sleeve and extending substantially from said base end of said elongated sleeve substantially to the other end of said elongated sleeve;
   flange means attached to said elongated sleeve adjacent said base end intermediate opposite ends of said air passageway and extending generally radially outwardly therefrom and operatively arranged with said air passageway for preventing both ends of said air passageway from being simultaneously insertable into a child's mouth; and
   means for removably retaining said device on said thumb.

2. The device of claim 1, wherein said air passageway has a cross-sectional shape comprising an open rectangle.

3. The device of claim 1, wherein said flange extends radially outwardly from said elongated sleeve for a portion of the circumference of said elongated sleeve such that when worn the portion of the elongated sleeve adjacent the index finger does not include said flange so that said flange does not substantially restrict movement of said thumb.

4. The device of claim 1, wherein said elongated sleeve comprises:
   two elongated members hingably attached to each other such that when said members are in a closed portion an elongated cylindrical opening is defined therebetween; and latch means for retaining said two elongated members in said closed position.

5. The device of claim 1, wherein said flange curves upwardly from said base end toward said end of said elongated sleeve opposite said base end.

6. A device worn on a thumb for the discouragement of thumb-sucking, said device comprising:

two elongated members, each of said members having a substantially open semi-circular cross-sectional shape;

at least one channel formed in said elongate members, said channel extending longitudinally from one end of said member to the other end;

hinge means longitudinally disposed on said two elongated members for connecting said two elongated members to each other such that when said two elongated members are in a closed position a substantially elongate cylindrical opening is defined therebetween to receive said thumb therein;

male latch means disposed on one of said elongated members;

female latch means disposed on the other of said elongated members such that said male latch means cooperates with said female latch means to selectively retain said two elongated members in said closed position;

flange means attached to each of said two elongated members adjacent corresponding ends thereof and extending generally outwardly therefrom, said flange means being sized and shaped such that when said two elongated members are in said closed position said flange means extends outwardly from a portion of the circumference of said closed elongated members at a position remote from the disstal tip of said thumb so as not to substantially restrict the movement of said thumb when said device is worn on said thumb, said flange means being operatively associated with said channel for preventing both ends of said channel from being simultaneously insertible into a child's mouth;

a first strap attached to one of said elongated members adjacent the end having said flange means, said first strap including a plurality of holes disposed along the length thereof; and a second strap attached to the other of said elongated members adjacent the end having said flange means, said second strap including a buckle cooperating with the holes of said first strap to selectively connect the free ends of said straps to each other, said straps being sized and shaped to wrap around the wrist of said child to selectively retain said device on said child's thumb.

* * * * *